(12) United States Patent
Grass et al.

(10) Patent No.: US 9,089,307 B2
(45) Date of Patent: Jul. 28, 2015

(54) THREE-DIMENSIONAL ANALYSIS OF LESIONS REPRESENTED BY IMAGE DATA

(75) Inventors: Michael Grass, Buchholz in der Nordheide (DE); Eberhard Sebastian Hansis, Menlo Park, CA (US); Thomas Buelow, Grosshansdorf (DE); Klaus Erhard, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 215 days.

(21) Appl. No.: 13/502,475

(22) PCT Filed: Oct. 21, 2010

(86) PCT No.: PCT/IB2010/054772
§ 371 (c)(1),
(2), (4) Date: Apr. 17, 2012

(87) PCT Pub. No.: WO2011/051863
PCT Pub. Date: May 5, 2011

(65) Prior Publication Data
US 2012/0207373 A1    Aug. 16, 2012

(30) Foreign Application Priority Data

Oct. 30, 2009    (EP) .................................... 09174567

(51) Int. Cl.
*G06K 9/00* (2006.01)
*A61B 6/00* (2006.01)
*A61B 6/02* (2006.01)
(Continued)

(52) U.S. Cl.
CPC .................. *A61B 6/502* (2013.01); *A61B 6/025* (2013.01); *A61B 6/466* (2013.01); *G06T 7/0012* (2013.01); *G06K 9/00208* (2013.01);
(Continued)

(58) Field of Classification Search
USPC ................. 382/128, 130, 131, 132, 219, 278; 128/922, 923
See application file for complete search history.

(56) References Cited

U.S. PATENT DOCUMENTS

| | | |
|---|---|---|
| 5,365,429 A | 11/1994 | Carman |
| 5,537,485 A | 7/1996 | Nishikawa et al. |

(Continued)

FOREIGN PATENT DOCUMENTS

WO    9928853 A1    6/1999

OTHER PUBLICATIONS

Jiang et al, "Malignant and Benign Clustered Microcalcifications: Automated Feature Analysis and Classification", Radiology, 1996, vol. 198, pp. 671-678.

(Continued)

*Primary Examiner* — Yosef Kassa

(57) ABSTRACT

A system for three-dimensional analysis of lesions in image data is disclosed. It comprises a lesion detection subsystem (1) for detecting individual lesions and three-dimensional positions of the individual lesions, based on e.g. breast image data (301). It comprises a cluster detection subsystem (2) for detecting a cluster of lesions (302), based on three-dimensional position information of lesions, and associating at least some of the individual lesions with the cluster of lesions (302), based on the three-dimensional positions of the individual lesions. The cluster detection subsystem (2) is arranged for detecting the cluster of lesions (302), based on the three-dimensional positions of the individual lesions. It comprises a cluster analysis subsystem (3) for analyzing the cluster of lesions (302).

15 Claims, 3 Drawing Sheets

(51) Int. Cl.
  *G06T 7/00* (2006.01)
  *G06K 9/62* (2006.01)

(52) U.S. Cl.
  CPC .... *G06K 9/6221* (2013.01); *G06T 2207/10072* (2013.01); *G06T 2207/30068* (2013.01)

(56) References Cited

U.S. PATENT DOCUMENTS

| | | | |
|---|---|---|---|
| 6,091,841 A | 7/2000 | Rogers et al. | |
| 6,246,782 B1 | 6/2001 | Shapiro et al. | |
| 7,469,056 B2* | 12/2008 | Ramm et al. | 382/128 |
| 7,519,210 B2* | 4/2009 | Hirsch et al. | 382/128 |
| 7,702,140 B2* | 4/2010 | Hirsch et al. | 382/128 |
| 7,783,089 B2 | 8/2010 | Kaufhold et al. | |
| 8,073,220 B2* | 12/2011 | Khamene et al. | 382/128 |
| 8,285,019 B2* | 10/2012 | Raundahl et al. | 382/128 |
| 8,306,601 B2* | 11/2012 | Lang et al. | 600/407 |
| 8,358,818 B2* | 1/2013 | Miga et al. | 382/128 |
| 8,414,892 B2* | 4/2013 | Cheung | 424/141.1 |
| 8,488,563 B2* | 7/2013 | Qi | 370/332 |
| 8,488,863 B2* | 7/2013 | Boucheron | 382/133 |
| 8,541,748 B2* | 9/2013 | Blevis | 250/363.02 |
| 8,620,055 B2* | 12/2013 | Barratt et al. | 382/131 |
| 8,634,617 B2* | 1/2014 | Tsougarakis et al. | 382/128 |
| 8,731,255 B2* | 5/2014 | El-Baz | 382/128 |
| 8,761,470 B2* | 6/2014 | Buelow | 382/128 |
| 8,824,762 B2* | 9/2014 | Rivaz et al. | 382/131 |
| 2001/0008562 A1 | 7/2001 | Rogers et al. | |
| 2007/0183641 A1 | 8/2007 | Peters et al. | |
| 2007/0280525 A1 | 12/2007 | Basilico et al. | |

OTHER PUBLICATIONS

Taylor et al, "Evaluation of a Decision Aid for the Classification of Microcalcifications" Proceedings of the 4th International Workshop on Digital Mammography, 1998, Document ms345, 9 Pages.

Constantinidis et al, "Evaluating Classification Strategies for Detection of Circumscribed Masses in Digital Mammograms", Image Processing and Its Applications, Conference Publication No. 465, 1999, pp. 435-439.

Yang et al, "3D Localization of Clustered Microcalcifications Using Cranio-Caudal and Medio-Lateral Oblique Views", Computerized Medical Imaging and Graphics, vol. 29, 2006, pp. 521-532.

* cited by examiner

THREE-DIMENSIONAL ANALYSIS OF LESIONS REPRESENTED BY IMAGE DATA

FIELD OF THE INVENTION

The invention relates to three-dimensional analysis of lesions represented by image data. The invention further relates to analysis of mammographic tomosynthesis image data. The invention further relates to analysis of a cluster of lesions.

BACKGROUND OF THE INVENTION

Tomosynthesis breast imaging may involve acquiring a plurality of tomosynthesis projection images at a series of angles relative to the breast, and using information describing at least some of these images to reconstruct a volumetric tomosynthesis reconstructed image. Such a volumetric image may comprise a stack of breast slices that have selective thicknesses and orientations and correspond to respective sections through or slices of the breast that typically are but need not be planar. In addition, conventional x-ray mammography images can be acquired, in the same procedure that acquires the tomosynthesis images of a breast or in a different procedure and in the same or different compressions of the breast. Such conventional images may be used in addition to the tomosynthesis images, to improve image analysis and display.

Tomosynthesis volume images can be processed by various techniques that draw attention to selected portions or features of these images, such as CAD (computer aided detection) techniques that may analyze the images to identify likely abnormalities and may place markers on a breast image or representation that identify the location and in some cases the type or other information about the likely abnormalities.

US 2009/0080752 A1 discloses a method of forming a set of candidate pixels that are candidates for inclusion in a final set of pixels that are determined to be associated with calcifications and called "calc pixels". The method includes eliminating from the set the candidate calc pixels that are not in a set of at least a specified number of candidate calc pixels in a specified volume of the 3D set of pixels, e.g., in a volume that represents a 1 cm by 1 cm by 3 mm volume of the breast, where the 3 mm is the size of a thick slice image.

SUMMARY OF THE INVENTION

It would be advantageous to have an improved three-dimensional analysis of lesions represented by image data. To better address this concern, a first aspect of the invention provides a system comprising:
 a lesion detection subsystem for detecting individual lesions and three-dimensional positions of the individual lesions, based on the image data; and
 a cluster detection subsystem for detecting a cluster of lesions, based on three-dimensional position information of lesions, and associating at least some of the individual lesions with the cluster of lesions, based on the three-dimensional positions of the individual lesions.

When applying this system, the three-dimensional positions of the individual lesions of a cluster of lesions become available. These three-dimensional positions may be used to derive information about the nature of the lesions. The relative positions of the lesions within the cluster may be used as an indication of a particular disease. The three-dimensional positions of the lesions in a cluster may be used as an input for a clinical decision support system, for example. If the lesions of a cluster are separately detected, it becomes possible to derive other characteristics of these lesions. Examples will be provided hereinafter. It is also possible to visualize the lesions schematically, based on the positions of the lesions. The lesions may comprise, for example, micro-calcifications. A cluster of lesions may comprise or consist of a plurality of lesions which are close to each other with respect to their positions in 3D. Existing lesion detection techniques may be used to detect the individual lesions. The image data may comprise breast image data and the lesions may comprise breast lesions such as micro-calcifications.

The cluster detection subsystem may be arranged for detecting the cluster of lesions, based on the three-dimensional positions of the individual lesions. In this case, the three-dimensional position information of lesions comprises the three-dimensional positions of the individual lesions. This way, existing clustering algorithms may be used to cluster the lesions. This may make the system easy to implement. Moreover, the developments in the fields of lesion detection and/or cluster detection may be re-used. This may lead to improved quality of the detected lesions and/or clusters. Moreover, using three-dimensional positions of lesions instead of individual pixels, allows using a cluster algorithm operating at a higher level of abstraction, because it does not have to handle individual pixels. This may improve the efficiency. The lesion detection subsystem may be arranged for detecting a plurality of lesions, regardless of whether they are part of the cluster or not. The cluster detecting subsystem may be arranged to receive the three-dimensional positions of these lesions as an input, and select the lesions which are part of a cluster from the plurality of lesions, based on the three-dimensional positions of the lesions. For example, k-means clustering or fuzzy c-means clustering may be used.

The lesion detection subsystem may be arranged for detecting lesions, based on at least one projection and at least one three-dimensional image of the lesions. Lesion detection can be performed in both the projection image and the three-dimensional image, using respective algorithms for lesion detection in projection images and three-dimensional images. The detection result may be combined for improving the robustness of the lesion detection, for example by improving specificity and/or sensitivity. A plurality of projections may be used to derive three-dimensional coordinates of lesions from the projections.

The system may comprise a cluster analysis subsystem for analyzing the cluster of lesions. Such analysis may be performed in many ways. Analysis of the cluster of lesions may reveal clinically relevant properties of the cluster of lesions.

The cluster analysis subsystem may comprise a surface generator for generating a circumscribing surface containing the cluster of lesions. The circumscribing surface may reveal the shape of the cluster. Such a shape may be associated with a particular region of the body. Also, the shape may be used as an indication of malignancy of the lesions. The system may comprise a visualization subsystem for visualizing the circumscribing surface. This allows the circumscribing surface to be inspected by a user of the system.

The cluster analysis subsystem may comprise a shape model subsystem for adapting a shape model to at least part of the cluster of lesions. The adapted shape model may comprise the circumscribing surface. An adaptive shape model is a useful way to model the cluster of lesions. The adaptive model may be used to derive further properties of the cluster of lesions, which may be useful for clinical diagnosis. Such properties may be the subject of a clinical decision support system.

The shape model may be associated with a region or structure of a breast. For example, a shape model associated with a duct may be used to assess the probability that the cluster of lesions is located in a duct. A relevant example of a duct in a breast is a milk duct.

The cluster analysis subsystem may comprise a statistical subsystem for determining a parameter of a statistical distribution associated with the cluster of lesions. Such a statistical subsystem may be able to compute a property with a relatively small computational effort.

The cluster analysis subsystem may comprise a distance computing subsystem for computing a distance between a pair of three-dimensional positions of lesions within the cluster. The distance between a pair of lesions within the cluster may be important in some clinical cases. For example, the maximal distance occurring between any pair of lesions in the cluster, or the average distance, may be relevant.

The cluster analysis subsystem may comprise a volume computing subsystem for computing a volume of a lesion within the cluster. Volume of the lesion may be an important parameter. Also, statistical information relating to the volumes of the lesions of the cluster may be computed.

The cluster analysis subsystem may comprise an absorption coefficient computing subsystem for computing an absorption coefficient of a lesion within the cluster. The absorption coefficient may also provide important information. Also, statistical information relating to the absorption coefficients of lesions of the cluster may be computed.

The cluster analysis subsystem may comprise a roughness coefficient computing subsystem for computing a roughness coefficient of a lesion within the cluster of lesions. Such a roughness coefficient may describe how rough or how smooth the surface of a lesion is.

The cluster analysis subsystem may comprise a shape computing subsystem for computing a shape of a lesion of the cluster of lesions. Such a shape may be related to malignancy; by combining information relating to the shapes of the lesions of a cluster, relevant information relating to the malignancy may be obtained.

The cluster detecting subsystem may be arranged for processing distances between pairs of three-dimensional positions of lesions. The distance between a pair of lesions may be an important criterion to decide whether they belong to a cluster.

The system may comprise a clinical decision support system for evaluating a characteristic of the three-dimensional cluster of lesions. The characteristics of a cluster of lesions may be relevant for diagnosis of breast diseases, or for deciding what action to take. Consequently, these characteristics may be suitable inputs for a clinical decision support system. The clinical decision support system may be coupled to the cluster analysis subsystem, for example an output of the cluster analysis subsystem may be used as an input of the decision support system.

The system may be part of a mammographic tomosynthesis image-forming apparatus. This allows integrating the image acquisition and the analysis of the images.

The system may also be part of a medical imaging workstation. Such a medical workstation may further comprise an input for receiving mammographic tomosynthesis image data. This allows integrating the system with other functionalities provided by the medical workstation.

An aspect of the invention provides a method of three-dimensional analysis of lesions represented by image data, comprising:

detecting individual lesions and three-dimensional positions of the individual lesions, based on the image data; and detecting a cluster of lesions, based on three-dimensional position information of lesions, and associating at least some of the individual lesions with the cluster of lesions, based on the three-dimensional positions of the individual lesions.

An aspect of the invention provides a computer program product comprising instructions for causing a processor system to perform the steps of the method.

It will be appreciated by those skilled in the art that two or more of the above-mentioned embodiments, implementations, and/or aspects of the invention may be combined in any way deemed useful.

Modifications and variations of the image acquisition apparatus, the workstation, the system, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

A lesion, as used in the present context, may be understood as an abnormality, such as a localized pathological change in a bodily organ or tissue. For example, lesions may comprise tiny flecks that are too small to be felt. They may be important markers of cancer that show up on ultrasound or mammogram. For example, micro-calcifications in a breast are an example of lesions. Lesions occurring in a breast may be referred to as breast lesions. Such breast lesions, in particular breast micro-calcifications, may be visible in mammography and/or mammographic tomosynthesis. However, this is not a limitation. Other kinds of lesions may be the subject of the system described herein.

Figure 1:
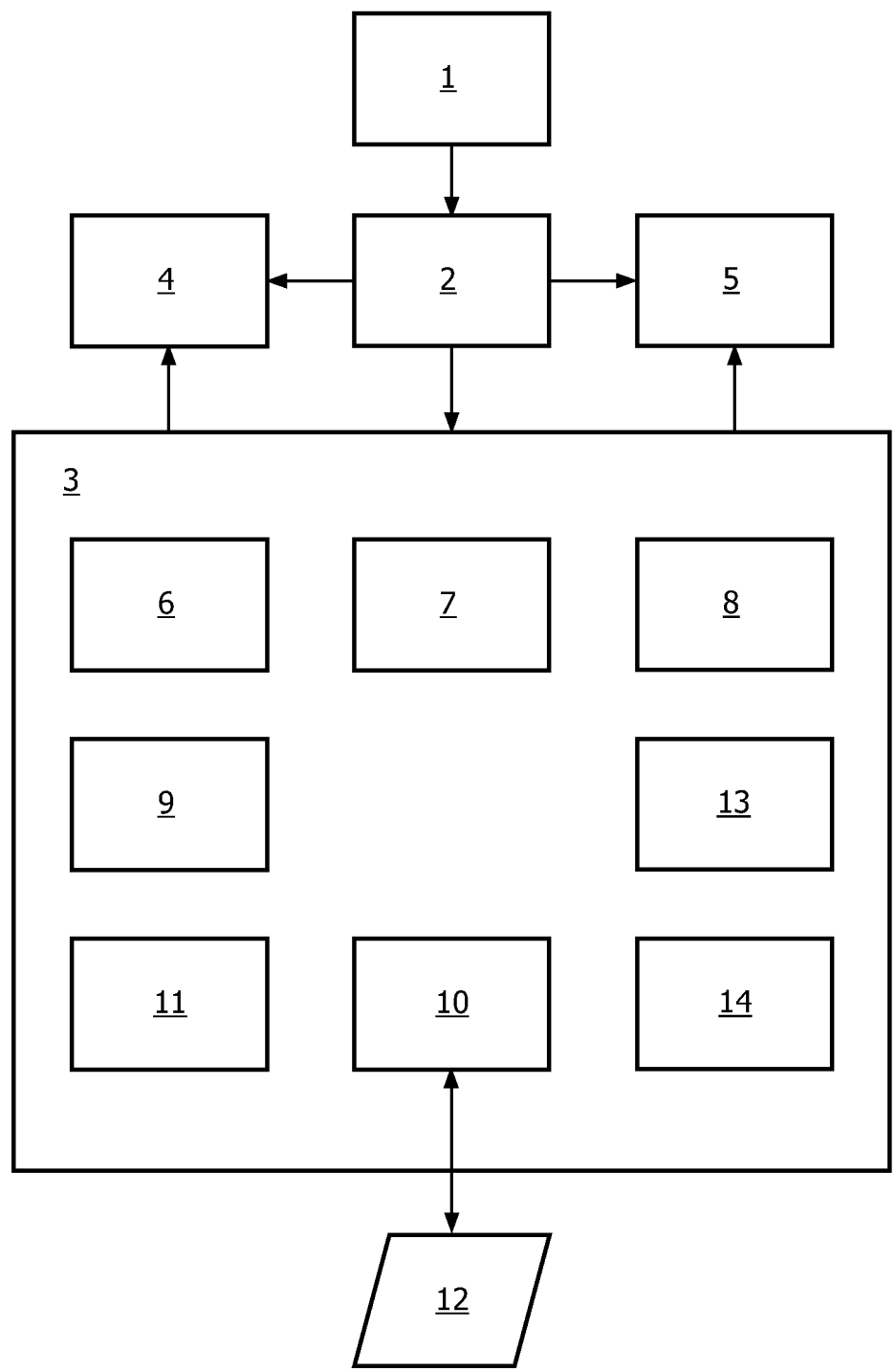
FIG. 1 is a block diagram of a system for three-dimensional analysis of lesions represented by image data.

FIG. 1 is a block diagram illustrating aspects of a system for three-dimensional analysis of breast micro-calcifications. Only elements relevant for this description have been illustrated. The system may be implemented, for example, using a suitably programmed microprocessor. For example, a computer program product is provided on a computer-readable medium, to implement the system in conjunction with the processor. Moreover, the system may comprise a memory for storing image data, a memory for storing software, a communications port for communicating with other devices, for example by means of wired or wireless network connection.

The communications port may be used to retrieve image data and/or to transmit data produced by the system. The system may further comprise a user input device for enabling a user to control the system, for example to initiate any of the steps of retrieving image data, detecting lesions in the image data, clustering lesions found in image data, outputting information of the lesions in a cluster, such as position information. The system may further comprise a display for visualizing the retrieved image data and/or information extracted about a cluster of lesions. The system may be implemented on a medical workstation, for example as a software option. The system may also be integrated in a medical image acquisition apparatus, such as a breast tomosynthesis scanner. The specific configuration of the system depicted in FIG. 1 should only be considered as an example implementation. Other designs of the system are within reach of the skilled person, in view of this description and claims.

The system may comprise a lesion detection subsystem 1 for detecting individual lesions and three-dimensional positions of the individual lesions, based on breast image data. The breast image data may be retrieved via the communications port and stored in local memory, for example. The image data may be obtained via an x-ray breast tomosynthesis acquisition apparatus. However, the image data may also be obtained via another imaging modality, such as magnetic resonance or CT. The lesions may be detected using a known lesion detection algorithm. An example of lesions which frequently occur in breasts is micro-calcifications. Such micro-calcifications may have a distinctive absorption coefficient, which helps in the lesion detection process. The lesion detection subsystem may be arranged for processing a volumetric dataset and detect the lesions directly in this three-dimensional volumetric dataset. For example, the detection may be based on local gray level and/or on a size and shape of an object having a distinct gray level range. Alternatively, the lesion detection subsystem may be arranged for detecting the lesions in a plurality of two-dimensional projection images. Such a lesion detection subsystem is described in "Scale-Space Signatures for the Detection of Clustered Microcalcifications in Digital Mammograms" by T. Netsch and H. -O. Peitgen, in IEEE Transactions on Medical Imaging, Vol. 18, No. 9, September 1999. By combining the detected lesions in the plurality of projection images, the three-dimensional positions of the lesions may be computed. In particular by detecting the same lesion in a plurality of projections acquired with different angular positions of the x-ray source and x-ray detector, the three-dimensional position of a lesion may be determined. This may be done using epi-polar geometry, as is known in the art per se. Other ways of detecting the plurality of lesions and the three-dimensional positions thereof may be used instead of the examples presented here. The lesion detection subsystem may be arranged for detecting the lesions, based on at least one projection and at least one three-dimensional image of the lesions. For example, by determining a probability that a structure is a lesion based on the 2D projection(s) and a probability that a structure is a lesion based on the 3D data sets, it is possible to form a combined probability that the structure is a lesion, based on both the 2D projection(s) and the 3D data set.

The lesion detection subsystem may have one or more user-selectable settings. These settings may be controlled by means of a user input device or by means of software. For example, in some cases it may be assumed that a lesion, such as a micro-calcification, is only visible in a number of the available projection images of a tomosynthesis dataset. A user-selectable setting could prescribe that only lesions which are visible in at least a minimum number of projections are taken into account. As another example, the size of the lesion could be subject to constraints such as a predefined minimum size.

The system may further comprise a cluster detection subsystem 2 for detecting a cluster of lesions, based on three-dimensional position information of lesions. For example, the pixel-based method described in US 2009/0080752 A1 may be used to detect a cluster. However, this is not a limitation. The detection of the cluster per se may be done independently from the individually recognized lesions, for example using a voxel-based analysis method. Such a voxel-based analysis method may first segment individual voxels as 'lesion voxels' and 'non-lesion voxels', and perform a clustering of the 'lesion voxels' to obtain a cluster of lesions. After that the individual lesions in the cluster may be identified and associated with the cluster. It is also possible to use the three-dimensional positions of the individual lesions to detect a cluster, as will be described hereinafter. Herein, a three-dimensional position of an individual lesion means a position of the lesion as a whole. For example, the center point or the point of gravity of a lesion could be used as the three-dimensional position of an individual lesion. The cluster detection subsystem 2 is arranged for associating at least some of the individual lesions with the cluster of lesions, based on the three-dimensional positions of the individual lesions. Consequently, the individual lesions which make up the cluster are associated with the cluster, making them available for further analysis. For example, the cluster detection algorithm may result in a three-dimensional region in which the cluster is located. The individual lesions inside this region may then be associated with the cluster. Alternatively, individual lesions may be analyzed by a cluster detection algorithm and the association between individual lesions and the cluster or clusters may be a natural result of the cluster detection algorithm.

For example, in the situation indicated by the arrow between the lesion detection subsystem 1 and the cluster detection subsystem 2, the lesion detection subsystem 1 may be first applied to a region of the image, or to the complete image, to detect a plurality of lesions, without prior knowledge of the cluster. Next, the cluster detection subsystem may be applied to detect the cluster of lesions. The cluster detection subsystem 2 may be arranged for detecting the cluster of lesions, based on the three-dimensional positions of the individual lesions. For example, the positions of the detected plurality of lesions may be analyzed to detect one or more clusters therein. When a cluster has been detected, the lesions making up the cluster may be associated with that cluster. The cluster detecting subsystem 2 may be arranged for selecting the lesions making up the cluster of lesions, based on the three-dimensional positions of the plurality of detected lesions.

The result of the lesion detection subsystem 1 and the cluster detection subsystem 2 may include a plurality of lesions making up a cluster of lesions, and three-dimensional positions of those lesions making up the cluster.

The cluster detection subsystem 2 may have one or more user-selectable settings. These settings may be controlled by means of a user input device or by means of software. For example, a maximum or variable distance or radius could be supplied which may limit the size of a cluster. It is also possible to search for a cluster having a particular shape. Such a shape may be configurable using parameters such as scale or length.

The system may comprise a cluster analysis subsystem 3 for analyzing the cluster of lesions. Such analysis may involve evaluating parameters of individual lesions making up the cluster of lesions. For example the three-dimensional positions of the individual lesions can play a role, as well as the sizes, volumes, shapes, gray values. Also, the total number of lesions within the cluster or the distances between the lesions within the cluster can play a role.

The cluster analysis subsystem may comprise a surface generator for generating a circumscribing surface containing the cluster of lesions. This surface may give a description of the overall shape of the cluster. An example of a circumscribing surface is a convex hull. However, other, non-convex, circumscribing surfaces are possible.

The system may further comprise a visualization subsystem 4. Such a visualization subsystem 4 may be arranged for providing a visualization of the cluster. For example, the visualization subsystem 4 may be arranged for visualizing the circumscribing surface. Other visualizations are possible, for example the individual lesions may be visualized.

Figure 3:
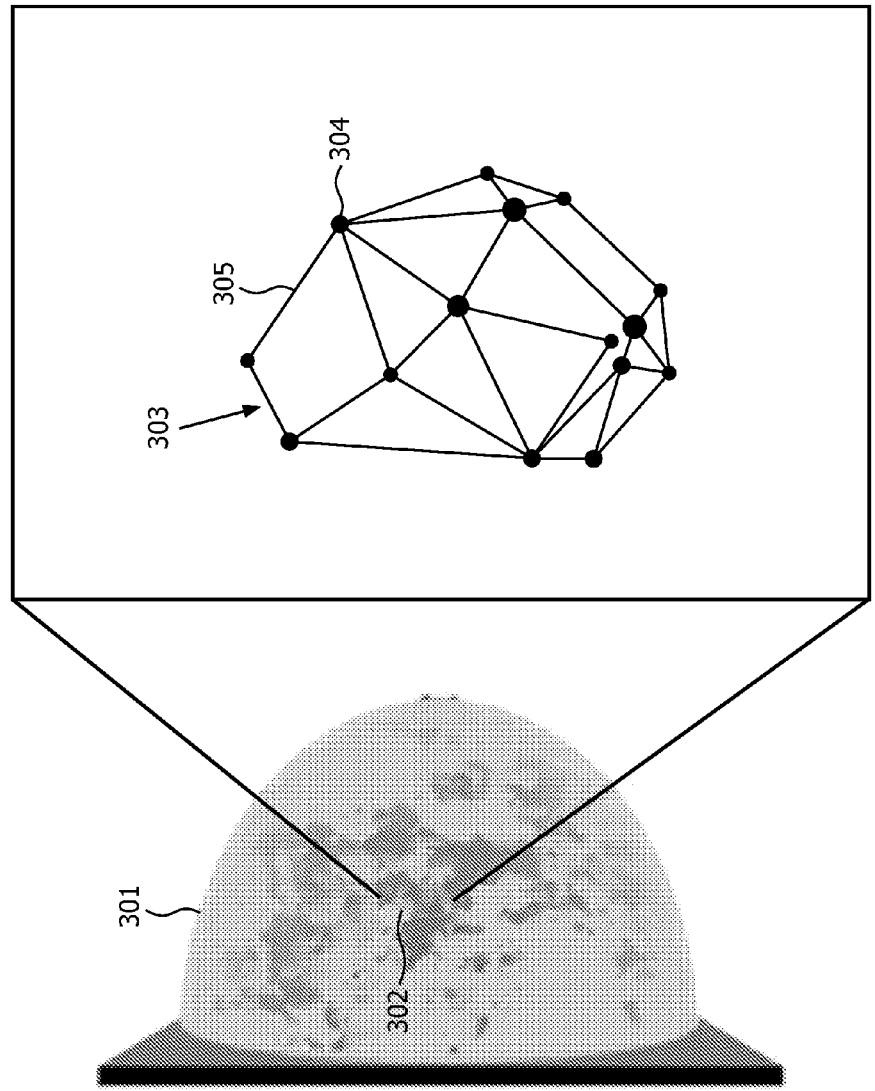
FIG. 3 is an illustration of a breast image and a cluster of lesions.

FIG. 3 is an example of a visualization 303 of a cluster of lesions 302. The lesions are represented by dots 304. Neighboring lesions are represented by lines 305. This gives an impression of the geometry of the cluster.

The cluster analysis subsystem 3 may comprise a shape model subsystem 10 for adapting a shape model to at least part of the cluster of lesions. A set of adaptive shape models 12 stored in a memory may be accessed by the shape model subsystem 10. These adaptive shape models 12 may be associated with anatomical areas or structures within the breast. For example, an adaptive shape model representing a tubular shape may be associated with a milk duct. When such a tubular shape can be fitted to the cluster, this may be an indication that the cluster is located in or around a milk duct.

The cluster analysis subsystem 3 may comprise a statistical subsystem 8 for determining a parameter of a statistical distribution associated with the cluster of lesions. In particular, statistical properties may be derived from quantities associated with individual lesions within the cluster. For example, mean and/or standard deviation of numerical properties of the individual lesions may be computed.

The cluster analysis subsystem 3 may comprise a distance computing subsystem 9 for computing a distance between a pair of three-dimensional positions of lesions within the cluster. Such a distance is illustrated graphically by the length of the line 305. The cluster analysis subsystem 3 may comprise a volume computing subsystem 7 for computing a volume of a lesion within the cluster. The cluster analysis subsystem 3 may comprise an absorption coefficient computing subsystem 11 for computing an absorption coefficient of a lesion within the cluster. The cluster analysis subsystem 3 may comprise a roughness coefficient computing subsystem 13 for computing a roughness coefficient of a lesion within the cluster of lesions. Such a roughness coefficient may comprise an indication of a roughness of the surface of a micro-calcification. The cluster analysis subsystem 3 may comprise a shape computing subsystem 14 for computing a shape of a lesion of the cluster of lesions. These five subsystems provide examples of parameters of individual lesions or pairs of lesions which may be the subject of the statistical subsystem 8 to obtain information about the cluster of lesions 302.

Moreover, the cluster detecting subsystem may be arranged for processing distances between pairs of three-dimensional positions of lesions. These distances may be used to detect a cluster. For example, a cluster may be detected when a number of lesions have pairwise distances below a predefined threshold.

The system may comprise a clinical decision support system 5 for evaluating a characteristic of the three-dimensional cluster of lesions. This characteristic may comprise any information described above. Such a characteristic may be derived from individual lesions of a cluster of lesions. The clinical support system 5 may be arranged for suggesting a next step in a patient flow in a healthcare organization. Clinical decision support systems are known in the art per se.

The system may be integrated in a mammographic tomosynthesis image-forming apparatus. Such apparatus is known in the art per se. The apparatus may comprise breast compression means. The apparatus may further comprise an x-ray source and an x-ray detector, which may be arranged to acquire mammographic projection images of the breast from a series of viewing angles. These images may be transformed into a volumetric image dataset, using known tomosynthesis techniques. The lesion detection may be performed by the lesion detection subsystem 1 directly in the two-dimensional projection images. By detecting the same lesion in a plurality of the projection images, the three-dimensional position of the lesion may be computed. Alternatively, the lesion may be detected in the volumetric image dataset, which may contain a three-dimensional representation of the lesion and which may provide the position information directly. These examples of image acquisition and reconstruction are not limiting. Other kinds of medical data may be used, including CT and MR.

The system may also be integrated in a medical imaging workstation. Such a workstation may receive mammographic tomosynthesis image data from an external source, for example via the communications port and/or network. The workstation may be arranged for performing the reconstruction of the volume image dataset from the projection images. The workstation may also be arranged for receiving the volume image dataset from the external source.

Figure 2:
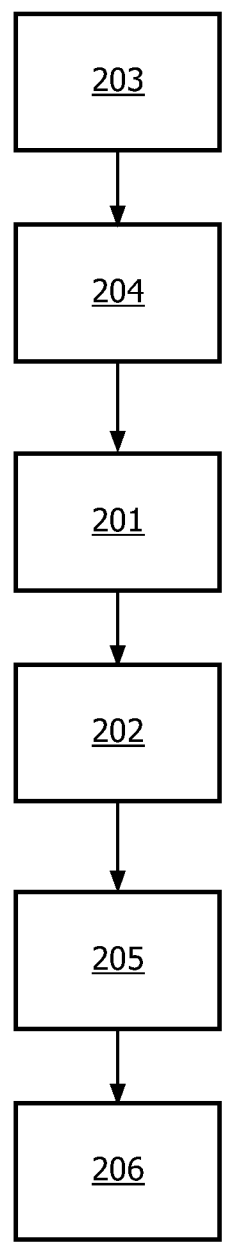
FIG. 2 is a flow diagram of a method of three-dimensional analysis of lesions represented by image data.

FIG. 2 is a flow chart illustrating a method of three-dimensional image analysis of lesions. The method comprises, in step 201, detecting individual lesions and three-dimensional positions of the individual lesions, based on breast image data. In step 202, the method comprises detecting a cluster of lesions, based on three-dimensional position information of lesions, and associating at least some of the individual lesions with the cluster of lesions, based on the three-dimensional positions of the individual lesions. The order of these two steps may be reversed depending on the particular embodiment, as described above. The method may commence in step 203 with acquiring the breast image data, followed by step 204 of reconstructing volumetric image data. Step 204 is optional, as it is possible to extract three-dimensional positions of lesions directly from two-dimensional projection images, as described above. Step 202 may be followed by step 205, in which cluster analysis may be performed as described above, and step 206, in which the results may be displayed. This is only an example method; other arrangements are possible, including changing the order in which some of the steps are performed. The method may be implemented by means of a computer program product comprising instructions for causing a processor system to perform the steps of the method. Such program product may be stored on a computer readable medium.

The application of tomosynthesis to X-ray mammography makes it possible to generate three-dimensional reconstructions of the micro-calcifications inside the breast. The three-dimensional spatial distribution can be determined. An approximate shape and density value of each calcification can be derived. The availability of this information enables new ways of 3D micro-calcification analysis for diagnostic purposes and lesion characterization. The shape and distribution of micro-calcifications or micro-calcification clusters may be considered relevant for tumor diagnostics in breast cancer.

Hereinafter, the particular case of micro-calcifications is described in more detail. However, this is not a limitation. The principles described can also be applied to other kinds of lesions. Micro-calcifications may be analyzed and/or visualized in a number of different ways. This applies to micro-calcifications detected in 3D tomosynthesis data, for example. The three-dimensional positions of calcifications may also be derived from other kinds of image data including a plurality of projection images. The detected micro-calcifications may be grouped into local or regional clusters of calcifications, using a clustering algorithm. The clustering algorithm can depend on a parameter that can be steered by the user interactively in order to define the clusters of physiologically related calcifications for further analysis.

Cluster(s) of micro-calcifications may be subjected to an analysis of distances between the different micro-calcifications and/or an analysis of the distribution of their 3D calcified volumes and absorption coefficients. The result of such analysis may be visualized.

Moreover, a circumscribing surface, for example a triangularized surface, containing all micro-calcifications inside a cluster, may be computed and/or visualized. This helps to get an impression of the outer shape of the cluster. Also, an analysis of the volume, size, and/or shape, inside which the calcifications are contained, may be obtained.

From the shape of the circumscribing surface it may be concluded which part of the anatomy contains the micro-calcifications. The localization process may be supported by adaptive shape models of the breast.

Three-dimensional clustering of micro-calcifications may provide improved 3D analysis of micro-calcifications inside the female breast, derivation of diagnostic quantities, or the ability for improved localization or characterization of a micro-calcification cluster in the breast.

Having the 3D spatial distribution of micro-calcifications available may help to determine in which breast compartment a tumor is located. If a cluster can be captured inside a tubular shape (for example, the circumscribing surface is tube-like) then it may be an indication that this tumor is inside a duct of the breast and therefore dangerous, while another distribution may support the relation to other compartments.

If the size and amount of calcifications in a cluster inside the breast are known, this can help to focus a biopsy in the breast or, for example, the size of resection.

FIG. 3 illustrates, schematically, a tomosynthesis image of a phantom breast 301 comprising a plurality of micro-calcifications. The micro-calcifications have been clustered, and a cluster 302 of micro-calcifications has been detected. The cluster 302 is displayed at 303. The visualization shows the individual micro-calcifications 304 having different sizes. Moreover, the visualization shows the connecting lines 305 between neighboring micro-calcifications 304 in the cluster 302, 303.

It will be appreciated that the invention also applies to computer programs, particularly computer programs on or in a carrier, adapted to put the invention into practice. The program may be in the form of a source code, an object code, a code intermediate source and object code, such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for three-dimensional analysis of lesions represented by image data, comprising:
a lesion detection subsystem for detecting individual lesions and three-dimensional positions of the individual lesions, based on the image data; and
a cluster detection subsystem for detecting a cluster of lesions, based on three-dimensional position information of lesions, and associating at least some of the individual lesions with the cluster of lesions based on the three-dimensional positions of the individual lesions,
wherein the cluster comprises a plurality of lesions grouped on the basis of a physical proximity of the lesions to each other.

2. The system according to claim 1, wherein the cluster detection subsystem is arranged for detecting the cluster of lesions, based on the three-dimensional positions of the individual lesions.

3. The system according to claim 1, wherein the lesion detection subsystem is arranged for detecting the lesions, based on at least one projection and at least one three-dimensional image of the lesions.

4. The system according to claim 1, further comprising a cluster analysis subsystem for analyzing the cluster of lesions.

5. The system according to claim 4, wherein the cluster analysis subsystem comprises a surface generator for generating a circumscribing surface containing the cluster of lesions.

6. The system according to claim 5, further comprising a visualization subsystem for visualizing the circumscribing surface.

7. The system according to claim 4, wherein the cluster analysis subsystem comprises a shape model subsystem for adapting a shape model to at least part of the cluster of lesions.

8. The system according to claim 7, wherein the shape model is associated with a region or structure of a breast.

9. The system according to claim 4, wherein the cluster analysis subsystem comprises at least one of:
   a distance computing subsystem for computing a distance between a pair of three-dimensional positions of lesions within the cluster of lesions;
   a volume computing subsystem for computing a volume of a lesion within the cluster of lesions;
   an absorption coefficient computing subsystem for computing an absorption coefficient of a lesion within the cluster of lesions;
   a roughness coefficient computing subsystem for computing a roughness coefficient of a lesion within the cluster of lesions; or
   a shape computing subsystem for computing a shape of a lesion of the cluster of lesions.

10. The system according to claim 1, wherein the cluster detecting subsystem is arranged for processing distances between pairs of three-dimensional positions of lesions.

11. The system according to claim 1, further comprising a clinical decision support system for evaluating a characteristic of the cluster of lesions.

12. A mammographic tomosynthesis image-forming apparatus comprising the system according to claim 1.

13. A medical imaging workstation comprising an input for receiving image data and the system according to claim 1.

14. A method of three-dimensional analysis of lesions represented by image data, comprising:
   detecting individual lesions and three-dimensional positions of the individual lesions, based on the image data; and
   detecting a cluster of lesions, based on three-dimensional position information of lesions, and associating at least some of the individual lesions with the cluster of lesions based on the three-dimensional positions of the individual lesions,
   wherein the cluster comprises a plurality of lesions grouped on the basis of a physical proximity of the lesions to each other.

15. A computer program product embodied on a non-transitory computer-readable medium comprising instructions for causing a processor system to perform the steps of the method according to claim 14.

* * * * *